United States Patent
Grover et al.

(10) Patent No.: US 11,432,891 B2
(45) Date of Patent: Sep. 6, 2022

(54) OFFSET INSTRUMENT DRIVE UNIT

(71) Applicant: Covidien LP, Mansfield, MA (US)

(72) Inventors: Simon R. Grover, Cambridge (GB);
Daniel L. Fuller, Haverhill (GB);
Charles F. Kilby, Cambridgeshire (GB)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/177,863

(22) Filed: Feb. 17, 2021

(65) Prior Publication Data
US 2021/0177533 A1 Jun. 17, 2021

Related U.S. Application Data

(63) Continuation of application No. 15/578,797, filed as application No. PCT/US2016/034509 on May 27, 2016, now Pat. No. 10,959,788.
(Continued)

(51) Int. Cl.
*A61B 34/30* (2016.01)
*A61B 34/35* (2016.01)
(Continued)

(52) U.S. Cl.
CPC ............ *A61B 34/30* (2016.02); *A61B 17/068* (2013.01); *A61B 34/00* (2016.02); *A61B 34/35* (2016.02);
(Continued)

(58) Field of Classification Search
CPC ................ A61B 34/30; A61B 34/70; A61B 2017/00477
See application file for complete search history.

(56) References Cited

U.S. PATENT DOCUMENTS

| 4,988,273 A | 1/1991 | Faig |
| 5,146,145 A | 9/1992 | Wood |

(Continued)

FOREIGN PATENT DOCUMENTS

| CN | 102119872 A | 7/2011 |
| CN | 104334111 A | 2/2015 |

(Continued)

OTHER PUBLICATIONS

Extended European Search Report issued in Application No. 16804085.5, dated Jan. 17, 2019 (10 pages).
(Continued)

*Primary Examiner* — Muhammad S Islam
*Assistant Examiner* — Devon A Joseph (57) ABSTRACT

A surgical system for selective connection to a robotic arm includes an instrument drive unit and a surgical instrument detachably coupled to the instrument drive unit. The instrument drive unit includes a first actuator, a linkage member having opposing first and second portions, and a drive member. The first portion of the linkage member is operatively coupled to the first actuator such that actuation of the first actuator moves the first portion in a first direction and the second portion in a second direction opposite of the first direction. The drive member is operatively coupled to the second portion of the linkage member. The surgical instrument includes a driven member operatively associated with the drive member of the instrument drive unit and an end effector operatively coupled with the driven member, wherein translation of the driven member effects a first function of the end effector.

20 Claims, 6 Drawing Sheets

Related U.S. Application Data (60) Provisional application No. 62/170,298, filed on Jun. 3, 2015.

(51) Int. Cl.
*A61B 34/00* (2016.01)
*A61B 17/068* (2006.01)
*A61B 17/00* (2006.01)

(52) U.S. Cl.
CPC .............. *A61B 34/70* (2016.02); *A61B 34/71* (2016.02); *A61B 2017/00473* (2013.01); *A61B 2017/00477* (2013.01)

(56) References Cited

U.S. PATENT DOCUMENTS

| | | | |
|---|---|---|---|
| 5,817,084 A | 10/1998 | Jensen | |
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,436,107 B1 | 8/2002 | Wang et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll et al. | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Joseph, III et al. | |
| 7,741,802 B2 | 6/2010 | Prisco et al. | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez et al. | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,337,515 B2 | 12/2012 | Viola et al. | |
| 8,347,757 B2 | 1/2013 | Duval | |
| 8,374,723 B2 | 2/2013 | Zhao et al. | |
| 8,418,073 B2 | 4/2013 | Mohr et al. | |
| 8,419,717 B2 | 4/2013 | Diolaiti et al. | |
| 8,423,182 B2 | 4/2013 | Robinson et al. | |
| 8,452,447 B2 | 5/2013 | Nixon | |
| 8,454,585 B2 | 6/2013 | Whitman | |
| 8,499,992 B2 | 8/2013 | Whitman et al. | |
| 8,508,173 B2 | 8/2013 | Goldberg et al. | |
| 8,528,440 B2 | 9/2013 | Morley et al. | |
| 8,529,582 B2 | 9/2013 | Devengenzo et al. | |
| 8,540,748 B2 | 9/2013 | Murphy et al. | |
| 8,551,116 B2 | 10/2013 | Julian et al. | |
| 8,562,594 B2 | 10/2013 | Cooper et al. | |
| 8,594,841 B2 | 11/2013 | Zhao et al. | |
| 8,597,182 B2 | 12/2013 | Stein et al. | |
| 8,597,280 B2 | 12/2013 | Cooper et al. | |
| 8,600,551 B2 | 12/2013 | Itkowitz et al. | |
| 8,608,773 B2 | 12/2013 | Tierney et al. | |

(56) References Cited

U.S. PATENT DOCUMENTS

| | | |
|---|---|---|
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,640,788 B2 | 2/2014 | Dachs, II |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | Patrick |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,555 B2 | 8/2016 | Kirschenman |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,737,371 B2 | 8/2017 | Romo |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 9,987,094 B2 | 6/2018 | Allen et al. |
| 10,008,017 B2 | 6/2018 | Itkowitz et al. |
| 10,016,900 B1 | 7/2018 | Meyer |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,130,427 B2 | 11/2018 | Tanner |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,470,830 B2 | 11/2019 | Hill |
| 10,485,621 B2 | 11/2019 | Morrissette et al. |
| 10,500,004 B2 | 12/2019 | Hanuschik et al. |
| 10,500,005 B2 | 12/2019 | Weir et al. |

(56) References Cited

U.S. PATENT DOCUMENTS

| | | |
|---|---|---|
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,959,788 B2 | 3/2021 | Grover et al. |
| 2006/0084945 A1 | 4/2006 | Moll et al. |
| 2008/0119870 A1 | 5/2008 | Williams |
| 2010/0204646 A1 | 8/2010 | Plicchi et al. |
| 2011/0118754 A1 | 5/2011 | Dachs, II et al. |
| 2011/0277775 A1 | 11/2011 | Holop et al. |
| 2012/0116416 A1 | 5/2012 | Neff et al. |
| 2013/0172713 A1* | 7/2013 | Kirschenman ......... A61B 34/30 600/585 |
| 2013/0325034 A1 | 12/2013 | Schena et al. |
| 2014/0005653 A1 | 1/2014 | Shelton, IV et al. |
| 2014/0222207 A1* | 8/2014 | Bowling ................ A61B 34/76 700/261 |
| 2014/0276761 A1 | 9/2014 | Parihar et al. |
| 2014/0303434 A1 | 10/2014 | Farritor et al. |
| 2015/0142013 A1 | 5/2015 | Tanner |
| 2015/0297199 A1 | 10/2015 | Nicholas et al. |
| 2016/0135914 A1* | 5/2016 | Isoda ..................... A61B 34/72 606/130 |
| 2016/0184032 A1 | 6/2016 | Romo |
| 2016/0346049 A1* | 12/2016 | Allen ..................... H02K 11/24 |
| 2017/0007336 A1 | 1/2017 | Tsuboi |
| 2017/0007342 A1 | 1/2017 | Kasai |
| 2018/0110576 A1 | 4/2018 | Kopp |

FOREIGN PATENT DOCUMENTS

| | | | |
|---|---|---|---|
| CN | 104349741 A | 2/2015 | |
| CN | 107735044 A | 2/2018 | |
| EP | 0705571 A1 | 4/1996 | |
| JP | H07194609 A | 8/1995 | |
| JP | 2003024336 A | 1/2003 | |
| JP | 2008036793 A | 2/2008 | |
| JP | 2013153295 A | 8/2013 | |
| JP | 2016514009 A | 5/2016 | |
| KR | 20120090410 A * | 2/2011 | ............ A61B 34/35 |
| WO | 2011060318 A1 | 5/2011 | |
| WO | 2013101269 A1 | 7/2013 | |
| WO | 2014163787 A1 | 10/2014 | |
| WO | 2015012023 A1 | 1/2015 | |
| WO | 2015088647 A1 | 6/2015 | |
| WO | 2016183054 A1 | 11/2016 | |

OTHER PUBLICATIONS

Chinese Office Action issued in Chinese Patent Application No. 201680031902.9, dated Dec. 3, 2019.

Japanese Office Action issued in Japanese Patent Application No. 2017-560974, dated Feb. 25, 2020.

* cited by examiner

OFFSET INSTRUMENT DRIVE UNIT

CROSS-REFERENCE TO RELATED APPLICATIONS

This application is a Continuation Application of U.S. patent application Ser. No. 15/578,797, filed on Dec. 1, 2017, which is a U.S. National Stage Application filed under 35 U.S.C. § 371 (a) of International Patent Application Serial No. PCT/US2016/034509, filed on May 27, 2016, which claims the benefit of and priority to U.S. Provisional Patent Application Ser. No. 62/170,298, filed on Jun. 3, 2015, disclosures of each of which are incorporated by reference herein.

BACKGROUND

Robotic surgical systems used in minimally invasive medical procedures include a console or cart supporting a robot arm and a surgical instrument having an end effector that may include, for example, forceps, a stapler, or a grasping tool. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult.

Accordingly, new robotic devices, systems, and methods that are reliable and that enable easy and efficient attachment and removal of surgical instruments would be desirable.

SUMMARY

The present disclosure describes robotic devices, systems, and methods that demonstrate a practical approach to meeting the performance requirements and overcoming the usability challenges associated with instrument attachment and removal. In general, the present disclosure describes robotic surgical systems that include an instrument drive unit and a surgical instrument support coupled to the instrument drive unit. The surgical instrument includes an end effector controllable to perform surgery in response to telemanipulation of actuators in the instrument drive unit.

In accordance with an embodiment of the present disclosure, there is provided a surgical system for selective connection to a robotic arm. The surgical system includes an instrument drive unit and a surgical instrument detachably coupled to the instrument drive unit. The instrument drive unit includes a first actuator, a linkage member having opposing first and second portions, and a drive member operatively coupled to the second portion of the linkage member. The first portion of the linkage member is operatively coupled to the first actuator such that actuation of the first actuator moves the first portion in a first direction and the second portion in a second direction opposite of the first direction. The surgical instrument includes a driven member operatively associated with the drive member of the instrument drive unit and an end effector operatively coupled with the driven member, wherein translation of the driven member effects a first function of the end effector.

In an embodiment, the linkage member may be pivotally supported about a pivot disposed between the first and second portions.

In another embodiment, the instrument drive unit may include a first elongate member having a first sleeve translatably mounted on the first elongate member. The first sleeve may be operatively associated with the first portion of the linkage member, such that rotation of the first elongate member pivots the linkage member about the pivot. In addition, the first sleeve may be threadably mounted on the first elongate member.

In another embodiment, the first sleeve may have a first camming pin and the first portion of the linkage member may define a first slot configured to slidably receive the first camming pin of the first sleeve, whereby translation of the first sleeve causes relative movement of the first camming pin within the first slot. Further, the first elongate member may include a pulley operatively coupled to the first actuator, wherein actuation of the first actuator causes rotation of the first elongate member.

In yet another embodiment, the instrument drive unit may further include a second elongate member having a second sleeve translatably mounted on the second elongate member. The second sleeve may be operatively associated with the second portion of the linkage member. In particular, the second sleeve may have a second camming pin, and the second portion of the linkage member may define a second slot configured to slidably receive the second camming pin of the second sleeve, whereby translation of the second sleeve causes relative movement of the second pin within the second slot.

In yet another embodiment, the surgical instrument may further include a first cable having a first end coupled to the driven member of the surgical instrument and a second end operatively associated with the end effector.

In an embodiment, the first actuator of the instrument drive unit may be controlled by telemanipulation.

In still another embodiment, the instrument drive unit may further include a second actuator and a rotatable member operatively coupled with the second actuator, and the surgical instrument may further include a gear member configured to operatively engage the rotatable member of the instrument drive unit and the end effector for concomitant rotation with the end effector.

In an embodiment, the first and second actuators may be independently actuatable.

In another embodiment, the instrument drive unit may be offset from a longitudinal axis defined by the robotic arm.

In yet another embodiment, the surgical instrument may include an elongate member extending distally from the driven assembly. The elongate member may support the end effector at a distal end of the elongate member.

In accordance with another aspect of the present disclosure, there is provided a robotic surgical assembly including a robotic arm having a mount, an instrument drive unit mounted on the mount of the robotic arm, and a surgical instrument detachably coupled to the instrument drive unit. The instrument drive unit includes a plurality of actuators, a plurality of linkage members, and a plurality of drive members. Each linkage member has opposing first and second portions. The first portion is operatively coupled to respective one of the plurality of actuators such that actuation of the respective one of the plurality of actuators moves the first portion in a first direction and the second portion in a second direction opposite of the first direction. Each one of the plurality of drive members is operatively coupled to the second portion of respective one of the plurality of linkage members. The surgical instrument includes a plurality of driven members and an end effector operatively coupled with the plurality of driven members. Each of the plurality of driven members is operatively associated with respective one of the plurality of drive members of the instrument drive unit, wherein translation of at least one of the plurality of driven members effects a first function of the end effector.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

Figure 1:
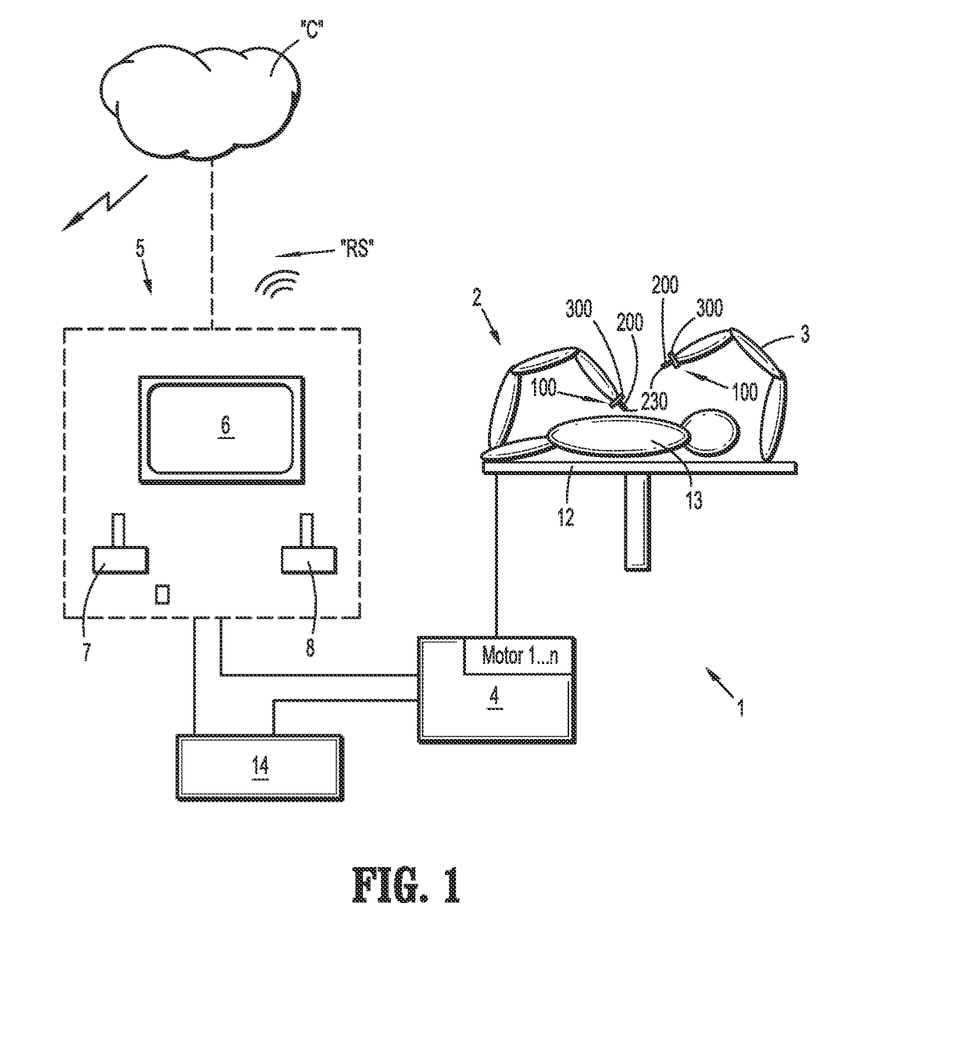
FIG. 1 is a schematic illustration of a robotic surgical system in accordance with the present disclosure.

With reference to FIG. 1, there is provided a robotic surgical system 1 including a plurality of robotic arms 2, 3; a control device 4; and an operating console 5 coupled with control device 4. Operating console 5 includes a display device 6 and manual input devices 7, 8, by means of which a person (not shown), for example, a surgeon, is able to telemanipulate robotic arms 2, 3.

Each of the plurality of robotic arms 2, 3 includes a plurality of members, which are connected through joints. Robotic surgical system 1 also includes a surgical assembly 100 connected to a distal end of each of robotic arms 2, 3. Surgical assembly 100 includes an instrument drive unit 300 and a surgical instrument 200 detachably coupled to instrument drive unit 300. Surgical instrument 200 includes an end effector 230.

Robotic arms 2, 3 may be driven by electric drives (not shown) that are connected to control device 4. Control device 4 (e.g., a computer) is set up to activate the drives, in particular by means of a computer program, in such a way that surgical assembly 100 of respective robotic arms 2, 3 executes a desired movement according to a movement defined by means of manual input devices 7, 8. Control device 4 may also be set up in such a way that it regulates movement of robotic arms 2, 3 and/or of the drives.

With continued reference to FIG. 1, robotic surgical system 1 is configured for use on a patient 13 lying on a patient table 12 for a minimally invasive procedure by means of end effector 230. Robotic surgical system 1 may include more than two robotic arms 2, 3. The additional robotic arms may also be connected to control device 4 and may be telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables coupled to end effector 230 of surgical instrument 200. While cables are shown and described, it is contemplated that cables can be replaced with rods or the like. In use, as these cables are pushed and/or pulled, the cables effect operation and/or movement of end effector 230 of surgical instrument 200. It is contemplated that control device 4 coordinates the activation of the various motors (Motor 1 . . . n) to coordinate a pushing or a pulling motion of one or more cables in order to coordinate an operation and/or movement of one or more end effectors 230. In embodiments, each motor can be configured to actuate a drive rod or a lever arm to effect operation and/or movement of end effectors 230 in addition to, or instead of, one or more cables.

Control device 4 can include any suitable logic control circuit adapted to perform calculations and/or operate according to a set of instructions. Control device 4 can be configured to communicate with a remote system "RS," either via a wireless (e.g., Wi-Fi™, Bluetooth®, LTE™, etc.) and/or wired connection. Remote system "RS" can include data, instructions and/or information related to the various components, algorithms, and/or operations of robotic surgical system 1. Remote system "RS" can include any suitable electronic service, database, platform, cloud "C", or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of robotic surgical system 1, such as through a driver circuit. Control device 4 can be configured to receive input signals and/or generate output signals to control one or more of the various components (e.g., one or more motors) of robotic surgical system 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS." Reference may be made to U.S. Patent Publication No. 2012/0116416, filed on Nov. 3, 2011, entitled "Medical Workstation," the entire content of which is incorporated herein by reference, for a detailed discussion of the construction and operation of robotic surgical system 1.

Figure 2:
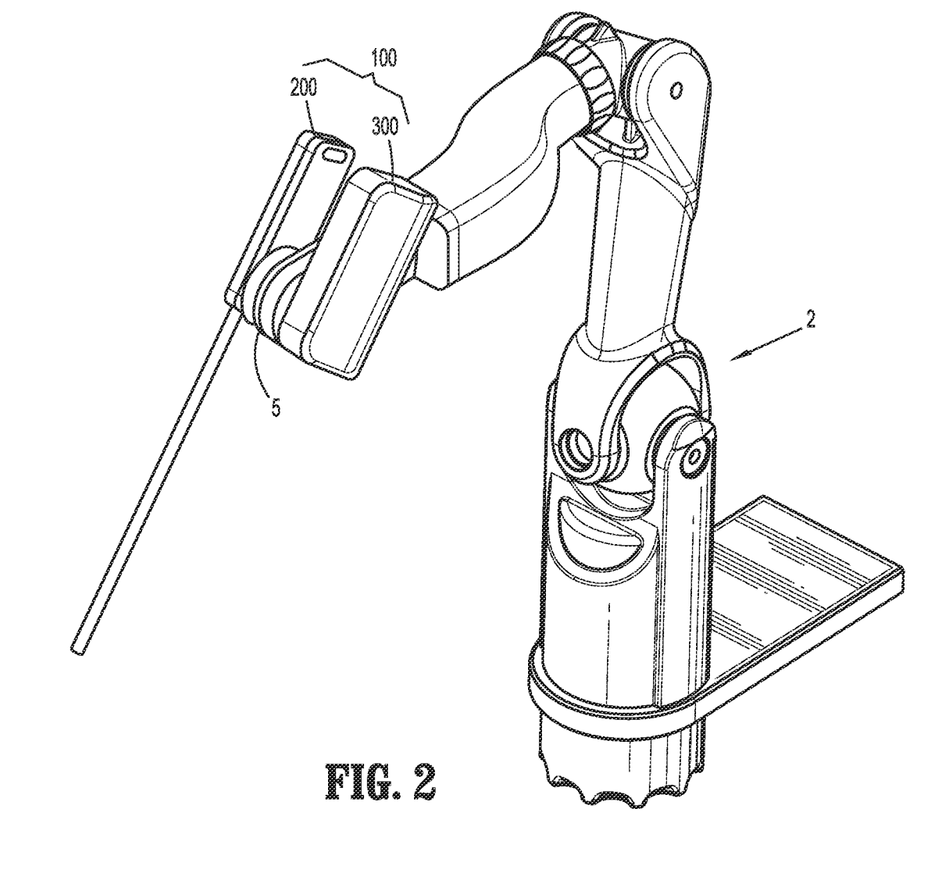
FIG. 2 is a perspective view of a robotic arm having a surgical assembly mounted thereon.
Figure 3:
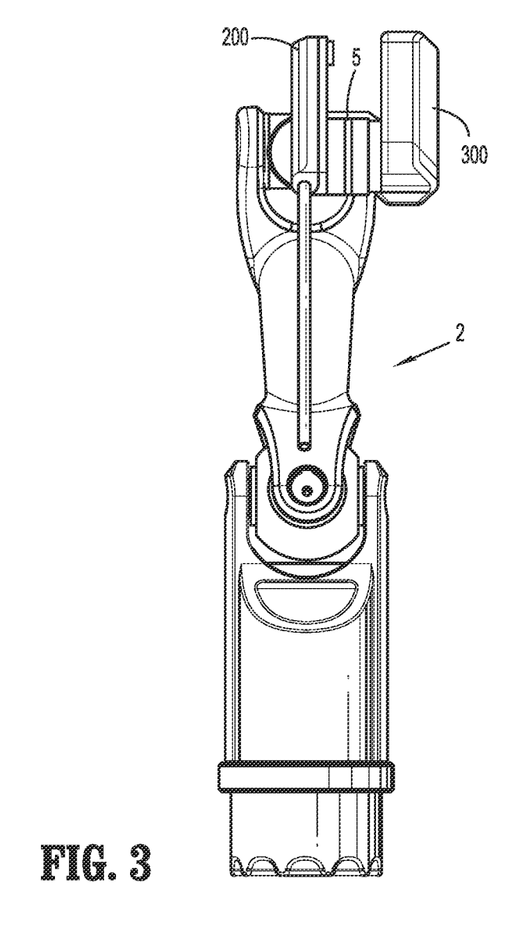
FIG. 3 is a front view of the robotic arm and the surgical assembly of FIG. 2.
Figure 4:
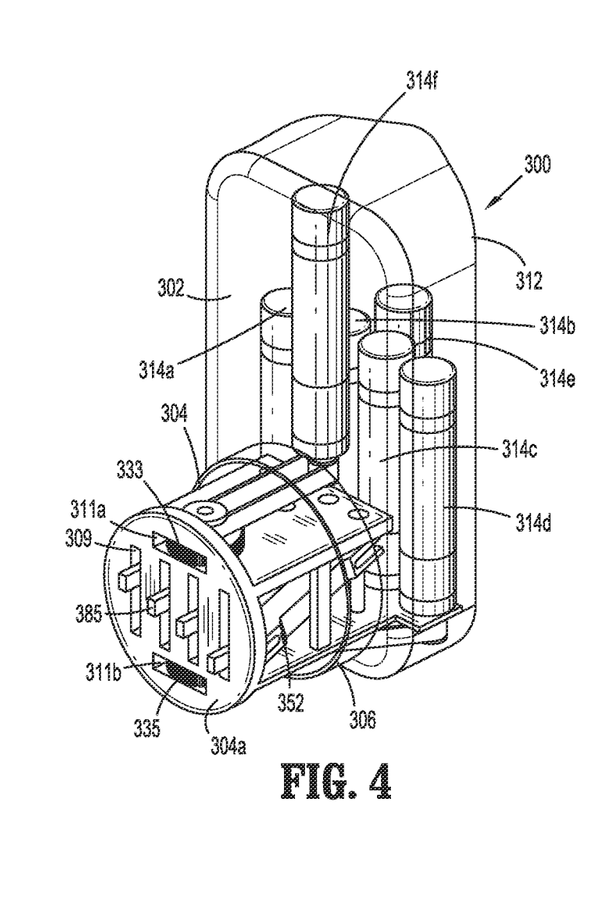
FIG. 4 is a perspective view of an instrument drive unit of the surgical assembly of FIG. 2 showing actuators and a drive system in phantom.

Turning now to FIGS. 2 and 3, surgical assembly 100 includes instrument drive unit 300 coupled to a mount 5 (FIG. 3) of robotic arm 2 and surgical instrument 200 releasably coupled to instrument drive unit 300. With reference now to FIG. 4, instrument drive unit 300 includes a body 312 having an actuation housing 302 and an adapter portion 304 extending transversely from actuation housing 302. Actuation housing 302 includes an annular rim 306 configured to securely support at least a portion of adapter portion 304 therein. Adapter portion 304 has a circular cross-section configured to extend through mount 5 of robotic arm 2. Adapter portion 304 includes an engaging surface 304a configured to operatively engage a portion of a contact surface 204 (FIG. 6) of surgical instrument 200.

Figure 5:
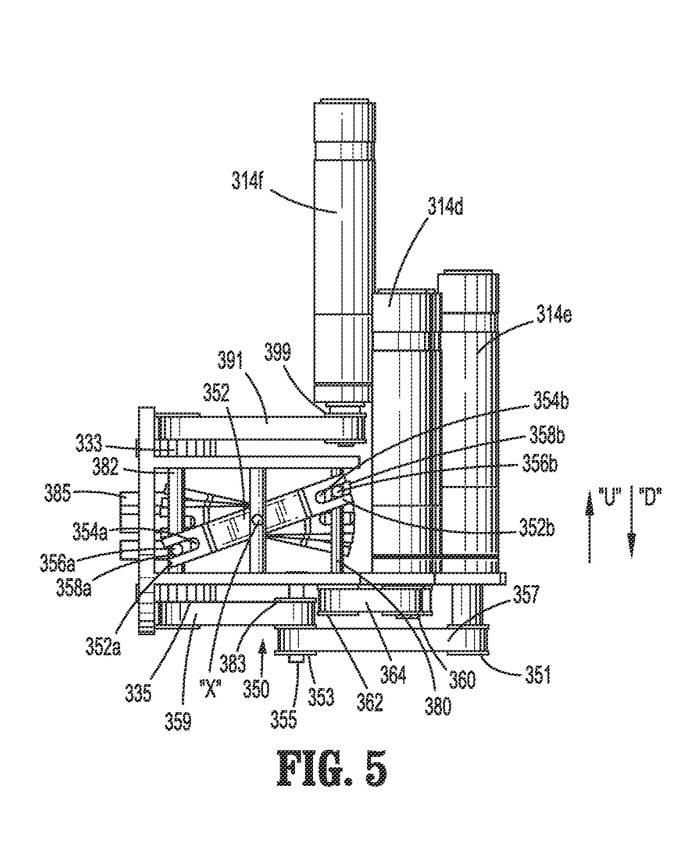
FIG. 5 is a side view of the actuators and the drive system of FIG. 4.

With reference now to FIGS. 4 and 5, actuation housing 302 supports a plurality of actuators or motors 314a-f. Adapter portion 304 includes a drive system 350 having a plurality of pivotably supported linkage members 352, a plurality of threaded members 380 (only one shown in FIG. 5), and a plurality of elongated members or shafts 382 (only one shown in FIG. 5). The plurality of pivotably supported linkage members 352 is configured to pivot about a common pivot "X". Each of the plurality of pivotably supported linkage members 352 includes opposing first and second portions 352a, 352b. Each of the plurality of threaded members 380 includes a sleeve or nut 358b threadably coupled with threaded member 380. Each of the plurality of elongated members 382 includes a sleeve 358a configured to slidably translate along respective elongated member 382.

Each of first and second portions 352a, 352b of linkage members 352 defines a slot 354a, 354b, respectively. Each slot 354a, 354b is configured to slidably receive a camming pin 356a of sleeve 358a and a camming pin 356b of sleeve 358b, respectively. Under such a configuration, rotation of threaded member 380 causes translation of sleeve 358b along respective threaded member 380. Translation of sleeve 358b along threaded member 380 causes relative movement between camming pin 356b and slot 354b and between camming pin 356a and slot 354a such that opposing first and second portions 352a, 352b move in opposite directions, as shown by arrows "D", "U" (FIG. 5), in the manner of a see-saw. Each of the plurality of sleeves 358a is connected to a respective one of a plurality of linear drives 385.

With continued reference to FIGS. 4 and 5, each of actuators or motors 314a-d includes a first pulley 360, and each of the plurality of threaded members 380 includes a second pulley 362. First pulley 360 and second pulley 362 are operatively coupled by a drive belt 364 such that rotation of first pulley 360 imparts rotation to second pulley 362. Rotation of second pulley 362 imparts concomitant rotation to threaded member 380, which in turn, causes translation of sleeve 358b along threaded member 380. Translation of sleeve 358b in, e.g., the direction of arrow "U", causes translation of sleeve 358a in the opposite direction, i.e., in the direction of arrow "D", to drive linear drive 385.

With particular reference back to FIG. 4, engaging surface 304a of adapter portion 304 defines a plurality of slots 309 configured to receive a respective linear drive 385 therein. Each linear drive 385 is slidable within respective slot 309 and extends through respective slot 309 such that each linear drive 385 engages a respective driven member 262a-d (FIG. 7) of surgical instrument 200, as will be described hereinbelow. In addition, engaging surface 304a further defines apertures 311a, 311b configured to receive gears 333, 335, respectively.

With particular reference to FIG. 5, actuator or motor 314e is coupled to a pulley 351 that is operatively coupled to a pulley 353 by a drive belt 357. Pulley 353 is secured to an elongate shaft 355 for concomitant rotation therewith. A pulley 383 is also secured to elongate shaft 355 for concomitant rotation therewith. Pulley 383 is operatively coupled to gear 335 by a second drive belt 359. Under such a configuration, actuation of actuator or motor 314e causes rotation of gear 335. At least a portion of gear 335 extends through aperture 311b (FIG. 4) such that gear 335 engages gear 227c of instrument interface 220 (FIG. 7) on surgical instrument 200, as will be discussed hereinbelow.

In addition, actuator or motor 314f is operatively coupled to pulley 399 that is coupled to gear 333 by a drive belt 391. Under such a configuration, actuation of actuator or motor 314f causes rotation of gear 333. At least a portion of gear 333 extends through aperture 311a (FIG. 4) for engagement with a gear 227b (FIG. 6) of instrument interface 220.

Figure 6:
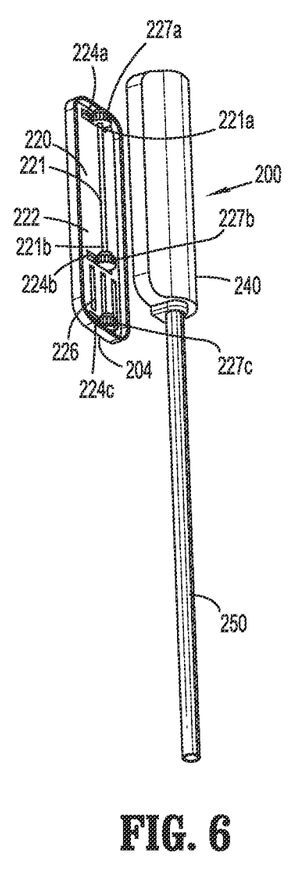
FIG. 6 is a perspective view of a surgical instrument of FIG. 2 showing an instrument interface detached from a driven assembly.
Figure 7:
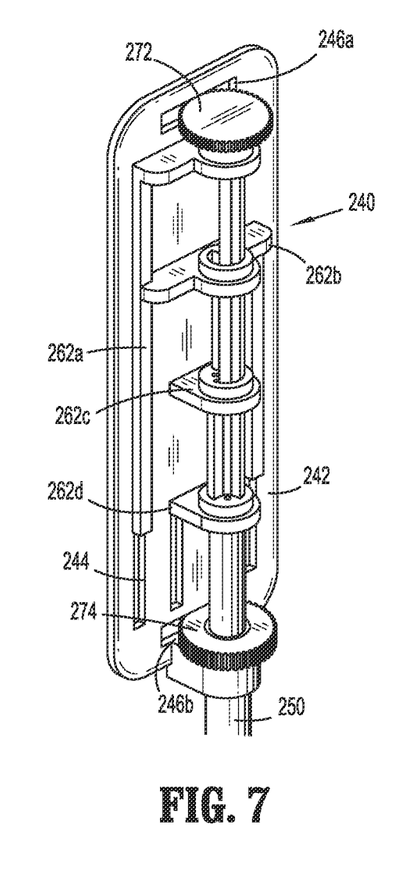
FIG. 7 is a perspective view of the driven assembly of FIG. 6 with a housing portion removed.

With reference now to FIGS. 6 and 7, a surgical instrument 200 includes an instrument interface 220, a driven assembly 240, and an elongate member 250, and an end effector 230 (FIG. 1) supported at a distal end of elongate member 250. Driven assembly 240 includes a support panel 242 defining a plurality of slots 244 along a length of support panel 242 and apertures 246a, 246b. Driven assembly 240 further includes a plurality of driven members 262a-d. A portion of each of the plurality of driven members 262a-d extends through a respective slot 244 and is translatable therewithin. Driven assembly 240 further includes gears 272, 274. At least a portion of each gear 272, 274 extends through a respective aperture 246a, 246b. Gear 274 is secured with elongate member 250 for concomitant rotation therewith.

With particular reference now to FIG. 6, instrument interface 220 includes a body panel 222 configured to be operatively mounted on driven assembly 240. Body panel 222 defines a plurality of apertures 224a-c and a plurality of slots 226. The plurality of apertures 224a-c are configured to receive at least a portion of a respective gear 227a-c therethrough. Each of the plurality of slots 226 aligns with a respective slot 244 of support panel 242 of driven assembly 240 such that a portion of each of the plurality of driven members 262a-d of driven assembly 240 extends through the respective slot 226 of instrument interface 220. The portion of each of the plurality of driven member 262a-d of driven assembly 240 operatively engages a respective linear drive 385 of instrument actuation drive 300. Under such a configuration, actuation of actuators or motors 314a-d causes translation of respective driven members 262a-d of driven assembly 240.

Each of the plurality of driven members 262a-d is coupled to a cable or rod (not shown) operatively associated with end effector 230 to effect a function of end effector 230. In particular, each cable may be coupled to end effector 230 such that actuation of each cable or combinations thereof performs a function of end effector 230. Longitudinal translation of one or more of cables may impart movement (e.g., rotation, pivoting, articulation, longitudinal/lateral translation, etc.) on end effector 230, or portions thereof. For instance, U.S. patent application Ser. No. 14/257,063, filed Apr. 21, 2014, and entitled "Adapter Assembly with Gimbal for Interconnecting Electromechanical Surgical devices and Surgical Loading Units, and Surgical Systems Thereof," the entire contents of which are hereby incorporated by reference, describes surgical stapling devices with end effectors that support distally advanceable sleds operatively coupled to a rotatable lead screw to fire surgical staples. Elongate member 250 is dimensioned to receive the plurality of cables and to enable each of the plurality of cables to linearly translate therethrough.

With continued reference to FIGS. 6 and 7, gear 227c of instrument interface 220 is configured to be aligned with and engage gear 274 of driven assembly 240. Gear 335 of instrument actuation device 300 is configured to engage gear 227c of instrument interface 220 such that actuation of actuator or motor 314e rotates gear 335 (FIG. 5), which in turn, rotates gear 227c of instrument interface 220 and gear 274 of driven assembly 240. Rotation of gear 274 of driven assembly 240 causes concomitant rotation of elongate member 250, which imparts rotation to end effector 230.

With particular reference to FIG. 6, instrument interface 220 further includes a rotatable shaft 221 having first and second ends 221a, 221b. First and second ends 221a, 221b include gears 227a, 227b respectively, for concomitant rotation with rotatable shaft 221. A portion of gear 227b extends through aperture 224b defined in body panel 222 and engages gear 333 of instrument drive unit 300. Under such a configuration, actuation of actuator or motor 314f causes rotation of gear 333, which in turn, imparts rotation to gear 227b. Rotation of gear 227b imparts concomitant rotation to gear 227a. Gear 227a of instrument interface 220 engages gear 272 of driven assembly 240. Gear 272 may be operatively coupled with end effector 230 to effect a function of end effector 230.

Figure 8:
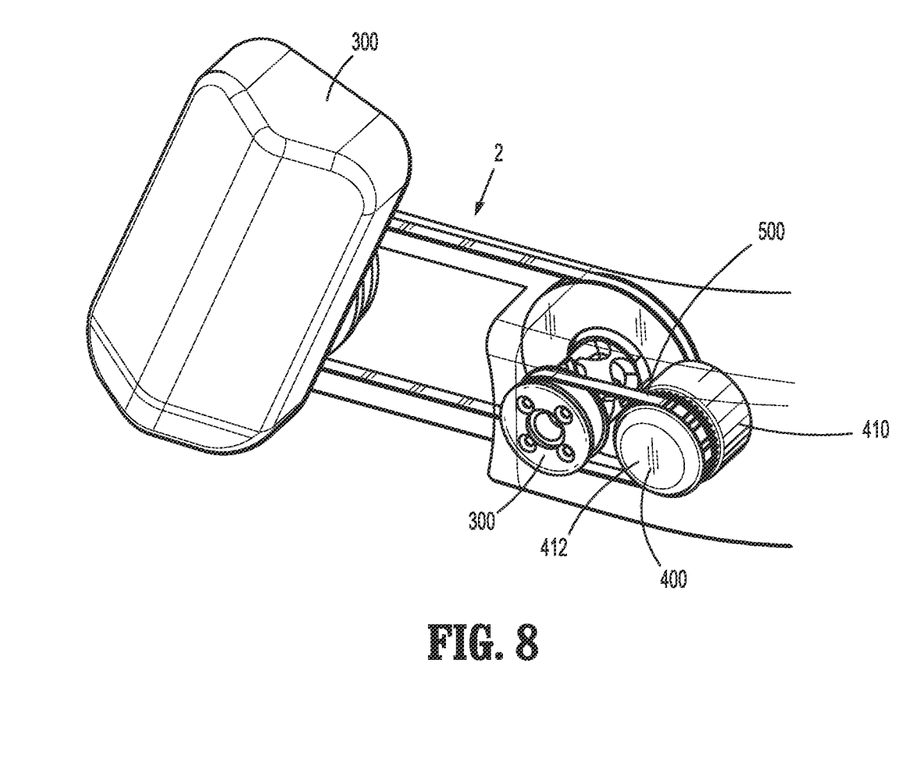
FIG. 8 is a perspective view of a torque sensor assembly for use with the robotic arm of FIG. 2.

With reference now to FIG. 8, robotic arm 2 supports a rotatable torque sensor 300 and a motor assembly 400 that are coupled together by a drive belt 500. Torque sensor 300 supports electrical components (e.g., resistors, wires, etc.) configured to communicate with control device 4 to provide torque feedback data, for example. Motor assembly 400 includes a motor 410 and a harmonic gear box 412 that cooperate to impart rotation on torque sensor 300 via drive belt 500 to effect rotation of instrument drive unit 300.

In operation, with reference to FIGS. 4-7, instrument drive unit 300 is mounted on mount 5 of robotic arm 2, and surgical instrument 200 is detachably coupled to instrument drive unit 300. Each linear drive 385 of instrument drive unit 300 engages respective driven member 262a-d of driven assembly 240 of surgical instrument 200. Further, gear 333 of instrument drive member 300 engages gear 227b of instrument interface 220 of surgical instrument 200. In addition, gear 335 of instrument drive unit 300 engages gear 227c of instrument interface 220 of surgical instrument 200. With surgical instrument 200 operatively coupled to instrument drive unit 300, one or more of the plurality of actuators or motors 314a-d are activated to rotate one or more of threaded member 380, which in turn, causes translation of one or more linear drives 385 of instrument drive unit 300. Actuation of one or more linear drives 385 causes translation of driven members 262a-d within slot 244 of support panel 242 of surgical instrument 200. Translation of driven members 262a-d translates the respective cable. Translation of cables, or combinations thereof, imparts movement (e.g., rotation, pivoting, articulation, longitudinal/lateral translation, etc.) on end effector 230, or portions thereof.

In addition, actuation of actuator or motor 314e causes rotation of gear 335, which in turn, imparts rotation to gear 227c of instrument interface 220. Rotation of gear 227c causes rotation of gear 274, which in turn, imparts concomitant rotation to elongate member 250. Rotation of elongate member 250 causes concomitant rotation of end effector 230. In addition, actuation of actuator or motor 314f causes rotation of gear 333 of instrument drive unit 300, which engages gear 227b of instrument interface 220 and causes rotation of gear 227b. Gear 227b imparts concomitant rotation to gear 227a of instrument interface 220. Gear 227a engages gear 272 of driven assembly 240. Under such a configuration, rotation of gear 227a of instrument interface 220 causes rotation of gear 272 of driven assembly 240. Gear 272 may be operatively coupled with end effector 230 to effect additional function of end effector 230.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system for selective connection to a robotic arm comprising:
   an instrument drive unit including:
      a first actuator;
      first elongate member defining a longitudinal axis and being supported for rotation about the longitudinal axis thereof, the first elongate member operatively coupled to the first actuator such that actuation of the first actuator rotates the first elongate member about the first longitudinal axis thereof;
      a first sleeve disposed about the first elongate member such that rotation of the first elongate member about the first longitudinal axis translates the first sleeve along the first longitudinal axis and along a length of the first elongate member; and
      a linkage member having opposing first and second portions and pivotally supported about a pivot disposed between the first and second portions, the first portion operatively coupled to the first sleeve such that actuation of the first actuator moves the first portion in a first direction and the second portion in a second direction opposite of the first direction; and
   a surgical instrument detachably coupled to the instrument drive unit, the surgical instrument including:
      a driven member operatively associated with the second portion of the instrument drive unit; and
      an end effector operatively coupled with the driven member such that mechanical input from the driven member effects a function of the end effector.

2. The surgical system according to claim 1, wherein the instrument drive unit further includes a second elongate member having a second sleeve translatable along a length of the second elongate member, the second sleeve operatively associated with the second portion of the linkage member.

3. The surgical system according to claim 2, wherein the second sleeve has a second camming pin, and the second portion of the linkage member defines a second slot configured to slidably receive the second camming pin of the second sleeve, whereby translation of the second sleeve causes relative movement of the second pin within the second slot.

4. The surgical system according to claim 1, wherein the first sleeve is threadably mounted on the first elongate member.

5. The surgical system according to claim 4, wherein the first sleeve has a first camming pin and the first portion of the linkage member defines a first slot configured to slidably receive the first camming pin of the first sleeve, whereby translation of the first sleeve causes relative movement of the first camming pin within the first slot.

6. The surgical system according to claim 1, wherein the first elongate member includes a pulley operatively coupled to the first actuator.

7. The surgical system according to claim 1, wherein the surgical instrument further includes a first cable having a first end coupled to the driven member of the surgical instrument and a second end operatively associated with the end effector.

8. The surgical system according to claim 1, wherein the first actuator of the instrument drive unit is controlled by telemanipulation.

9. The surgical system according to claim 1, wherein the instrument drive unit further includes a second actuator and a rotatable member operatively coupled with the second actuator, and the surgical instrument further includes a gear member configured to operatively engage the rotatable member of the instrument drive unit and the end effector for concomitant rotation with the end effector.

10. The surgical system according to claim 9, wherein the first and second actuators are independently actuatable.

11. The surgical system according to claim 1, wherein the instrument drive unit is offset from a longitudinal axis defined by the robotic arm.

12. The surgical system according to claim 1, wherein the surgical instrument includes an elongate member supporting the end effector at a distal end of the elongate member.

13. A robotic surgical assembly comprising:
a robotic arm having a mount;
an instrument drive unit mounted on the mount of the robotic arm, the instrument drive unit including:
a plurality of actuators;
a plurality of first elongate members, each first elongate member of the plurality of first elongate members defining a respective longitudinal axis and each being supported for rotation about the respective longitudinal axis thereof, each first elongate member including a first sleeve such that rotation of the first elongate member about the longitudinal axis thereof causes axial displacement of the first sleeve along the respective longitudinal axis and axially along the first elongate member;
a plurality of second elongate members, each second elongate member of the plurality of second elongate members including a second sleeve slidably supported thereon; and
a plurality of linkage members, each linkage member having opposing first and second portions and pivotally supported about a pivot disposed between the first and second portions that are axially aligned, the first portion operatively coupled to the corresponding first sleeve such that rotation of the corresponding first elongate member of the plurality of first elongate members moves the first portion in a first direction and the second portion in a second direction opposite of the first direction, the second portion operatively coupled to the second sleeve of a corresponding second elongate member of the plurality of second elongate members such that the first and second portions move along respective lengths of the corresponding first and second elongate members; and
a surgical instrument detachably coupled to the instrument drive unit, the surgical instrument including a plurality of driven members, each driven member of the plurality of driven members operatively associated with the second portion of corresponding one of the plurality of linkage members of the instrument drive unit, wherein translation of at least one of the plurality of driven members effects a function of the surgical instrument.

14. The robotic surgical assembly according to claim 13, wherein rotation of the first elongate member pivots the corresponding one of the plurality of linkage members about the pivot.

15. The robotic surgical assembly according to claim 14, wherein each first sleeve is threadably mounted on the corresponding first elongate member.

16. The robotic surgical assembly according to claim 15, wherein the first sleeve has a first camming pin, and the first portion of the corresponding linkage member defines a first slot configured to slidably receive the first camming pin, whereby translation of the first sleeve along the first elongate member causes relative movement of the first camming pin within the first slot.

17. The robotic surgical assembly according to claim 13, wherein each first elongate member of the plurality of first elongate members includes a pulley operatively coupled to the first actuator, wherein actuation of the first actuator causes rotation of the first elongate member.

18. The robotic surgical assembly according to claim 17, wherein each second elongate member of the plurality of second elongate members includes a second sleeve translatably mounted on the corresponding second elongate member, the second sleeve operatively associated with the second portion of the corresponding linkage member.

19. The robotic surgical assembly according to claim 18, wherein the second sleeve has a second camming pin, and the second portion of the corresponding linkage member defines a second slot configured to slidably receive the second camming pin, whereby translation of the second sleeve causes relative movement of the second pin within the second slot.

20. A surgical system for selective connection to a robotic arm comprising:
an instrument drive unit including:
first elongate member defining a first longitudinal axis and being supported for rotation about the first longitudinal axis thereof;
a first sleeve disposed about the first elongate member such that rotation of the first elongate member about the first longitudinal axis translates the first sleeve along the first longitudinal axis and along a length of the first elongate member; and
a linkage member operatively coupled to the first sleeve such that rotation of the first elongate member pivots the linkage member; and
a surgical instrument detachably coupled to the instrument drive unit, the surgical instrument including:
a driven member operatively associated with the linkage member of the instrument drive unit; and an end effector operatively coupled with the driven member such that mechanical input from the driven member effects a function of the end effector.

\* \* \* \* \*